(12) United States Patent
Putzer

(10) Patent No.: US 7,491,193 B2
(45) Date of Patent: Feb. 17, 2009

(54) PERSONAL CARE APPARATUS WITH AT LEAST TWO SUCTION NOZZLES

(75) Inventor: Arthur Putzer, Bad Eisenkappel (AT)

(73) Assignee: Koninklijke Philips Electronics N.V., Eindhoven (NL)

( * ) Notice: Subject to any disclaimer, the term of this patent is extended or adjusted under 35 U.S.C. 154(b) by 1157 days.

(21) Appl. No.: 10/317,570

(22) Filed: Dec. 12, 2002

(65) Prior Publication Data

US 2003/0114804 A1 Jun. 19, 2003

(30) Foreign Application Priority Data

Dec. 17, 2001 (EP) .................................. 01000762

(51) Int. Cl.
*A61M 1/00* (2006.01)

(52) U.S. Cl. ........................ 604/313; 604/314; 604/315; 604/316; 604/119; 604/268; 604/264; 604/257; 604/261; 604/289; 604/34; 604/35; 604/275; 604/276; 604/94.01; 604/902; 34/642; 34/251; 34/541; 239/695; 239/696; 239/700

(58) Field of Classification Search ................. 604/313, 604/289, 314, 315, 316, 119, 268, 264, 257, 604/261, 34, 35, 275, 276, 902, 94.01, 118; 34/642, 251, 541; 15/322, 354, 414, 415, 15/416; 239/695, 696, 700

See application file for complete search history.

(56) References Cited

U.S. PATENT DOCUMENTS

| | | | | |
|---|---|---|---|---|
| 1,499,937 A | * | 7/1924 | Leathers | 417/159 |
| 2,076,410 A | * | 4/1937 | McGerry | 601/108 |
| 2,100,185 A | * | 11/1937 | Engstrand | 417/170 |
| 2,225,789 A | * | 12/1940 | Metcalfe et al. | 417/193 |
| 3,896,810 A | * | 7/1975 | Akiyama | 604/117 |
| 4,195,780 A | * | 4/1980 | Inglis | 239/73 |
| 4,692,140 A | * | 9/1987 | Olson | 604/40 |
| 5,024,615 A | | 6/1991 | Buchel | 604/119 |
| 5,249,610 A | * | 10/1993 | Cassou et al. | 141/130 |
| 5,326,237 A | * | 7/1994 | Cecil et al. | 417/511 |
| 5,377,701 A | * | 1/1995 | Fang | 132/271 |
| 5,836,944 A | * | 11/1998 | Cosmescu | 606/41 |
| 6,019,749 A | * | 2/2000 | Fields et al. | 604/313 |
| 6,042,341 A | * | 3/2000 | Richter | 417/151 |
| 6,319,211 B1 | * | 11/2001 | Ito et al. | 601/7 |
| 6,673,081 B1 | * | 1/2004 | Tavger et al. | 606/131 |
| 2005/0096607 A1 | * | 5/2005 | Beck | 604/264 |

FOREIGN PATENT DOCUMENTS

| | | |
|---|---|---|
| EP | 0152390 A2 | 2/1985 |
| EP | 0997156 | 5/2000 |

* cited by examiner

*Primary Examiner*—Tatyana Zalukaeva
*Assistant Examiner*—Ginger T Chapman

(57) ABSTRACT

A personal care apparatus (1) is provided with a suction nozzle configuration (4) which has two different suction nozzles (15, 22) with two different suction sections (27, 26), wherein the suction nozzles (15, 22) are held adjustably in relation to each other along a path of motion (16) which is preferably perpendicularly to their suction sections (27, 26), so that by means of an adjustment of this type in each case one of the suction nozzles (15, 22) may be adjusted with its suction section (27, 26) into an operating position permitting suctorial interaction with an area of the skin.

14 Claims, 3 Drawing Sheets

FIG.1

PERSONAL CARE APPARATUS WITH AT LEAST TWO SUCTION NOZZLES

The invention relates to a personal care apparatus with an air pump and with a suction nozzle configuration which has an air connection to the air pump and which has at least two suction nozzles having suctions sections of different sizes wherein in a plan view suction sections, the suction section of one suction nozzle lies within the suction section of a suction nozzle having a is larger suction section.

The invention also relates to a suction nozzle configuration for a personal care apparatus, which suction nozzle configuration has at least two suction nozzles with different suction sections, with, in a plan view of the suction sections, the suction section of one suction nozzle lying within the suction section of a suction nozzle having a larger suction section.

Personal care apparatus conforming to the aforesaid embodiment described in the first paragraph and a suction nozzle configuration conforming to the aforesaid embodiment described in the second paragraph are known from the patent EP 0 997 156 A2. In the known embodiment, the suction nozzle configuration has a disk-shaped center part from which, in a first direction, a first suction nozzle and, in a second direction opposed to the first direction, a second suction nozzle protrude, so the suction sections of the two suction nozzles face away from each other. In the known personal care apparatus, the known suction nozzle may be plugged onto a suction port in the personal care apparatus in two locations facing each other to enable in each case one of the two suction nozzles, which differ with regard to their suction sections, to be brought into an active suctorial connection with an area of the skin. In order to achieve a change of the achievable suction effect with the known personal care apparatus by means of the suction nozzles having different suction sections, the known suction nozzle must be removed from the suction port in the personal care apparatus and then replaced on the suction port in a reversed position. This represents a relatively laborious handling method. In addition, with the known personal care apparatus, it is imperative that the suction nozzle configuration is designed to be removable from the suction port in order to enable it to be plugged onto the suction port in two mutually reversed positions, but this means there is a risk that the suction nozzle configuration may undesirably slide down from the suction port, which may lead to an undesirable loss of the suction nozzle configuration.

It is the object of the invention to avoid the aforesaid problems and to realize an improved personal care apparatus and an improved suction nozzle configuration.

To achieve the aforesaid object, a personal care apparatus according to the invention is provided with features according to the invention so that the personal care apparatus according to the invention may be characterized as follows:

Personal care apparatus with an air pump and with a suction nozzle configuration which has an air connection to the air pump and which has at least two suction nozzles, with suction sections of different sizes, wherein, in a plan view of the suction sections, the suction section of one suction nozzle lies within the suction section of a suction nozzle having a larger suction section, and wherein all suction sections of the suction nozzles face away from the rest of the personal care apparatus, and wherein the suction nozzles are held adjustably with regard to each other along a path of motion, and wherein, it is possible to adjust at least one of said suction nozzles into an operating position enabling suctorial interaction with an area of the skin by means of an adjustment of suction nozzles in relation to each other.

To achieve the aforesaid object, a suction nozzle configuration according to the invention is provided with features according to the invention, so that a suction nozzle configuration according to the invention may be characterized as follows:

A suction nozzle configuration for a personal care apparatus, which suction nozzle configuration has at least two suction nozzles with suction sections of different sizes, wherein, in a plan view of the suction sections, the suction section of one suction nozzle lies within the suction section of a suction nozzle having a larger suction section, and wherein all suction sections of suction nozzles face away from the rest of the personal care apparatus, and wherein the suction nozzles are held adjustably in relation to each other along a path of motion, and wherein it is being possible to adjust at least one of said suction nozzles into an operating position permitting suctorial interaction with an area of the skin by an adjustment of suction nozzles in relation to each other.

The provision of the features according to the invention achieves in a structurally simple manner and with simple means that the suction sections of at least two suction nozzles in a suction nozzle configuration may be optionally brought into an active connection with an area of the skin to be treated without having to separate the suction nozzle configuration from the personal care apparatus. In addition, this achieves the advantage that a suction nozzle configuration may be realized which may have not only two suction nozzles, but also more than two suction nozzles, for example three suction nozzles. If more than two suction nozzles are provided, the embodiment may be designed in such a way that, after an adjustment of at least one suction nozzle, two other suction nozzles with their suction sections can interact with an area of the skin at the same time. In addition, according to the invention the advantage is achieved that, if desired, the suction nozzle configuration may be connected to the personal care apparatus inseparably or may only be detached after undoing a locking device which is to be deliberately actuated. In addition, according to the invention the advantage is achieved that a particularly quick change between at least two suction nozzles is enabled, a change of this type between at least two suction nozzles also being possible during a suction operation.

As already mentioned, in one solution according to the invention, more than two suction nozzles may be provided on one suction nozzle configuration. However, it has been found to be sufficient in many applications, if only two suction nozzles are provided in one suction nozzle configuration. Here, an embodiment may be designed such that that an external suction nozzle has a fixed connection to a component of the personal care apparatus, while an internal suction nozzle essentially arranged within the external suction nozzle is held adjustably in relation to the external suction nozzle. However, it has been found to be very advantageous if the internal suction nozzle with a smaller suction section has a fixed connection to at least one holding part of the personal care apparatus, and the external suction nozzle with a larger suction section has an adjustable connection to the internal suction nozzle. An embodiment of this type has been found to be particularly advantageous with regard to obtaining as simple a handling as possible. In addition, an embodiment of this type is advantageous because this achieves a simple establishment of a permanent and reliable air-tight connection with to air pump. In addition, an embodiment of this type is advantageous because it achieves simple detachability of the external suction nozzle from the internal suction nozzle for cleaning purposes.

In the solution according to the invention as described in the previous paragraph, the adjustment of the external suction nozzle in relation to the internal suction nozzle may be achieved in such a way that the external suction nozzle is displaced in relation to the internal suction nozzle with the aid of at least one finger. However, it has been found to be particularly advantageous if, in addition, an adjusting ring (28) which is essentially perpendicular to the path of motion (16) is rotatable supported on the internal suction nozzle (15), and wherein adjusting means (31) for the adjustment of the external suction nozzle (22) are provided between the adjusting ring (28) and the external suction nozzle (22). This achieves a particularly smooth and uniform and simple adjustment of the external suction nozzle in relation to the internal suction nozzle.

In the above-described context, it has been found to be particularly advantageous if, in addition, the adjusting means (31) are formed by a pin-slot configuration which has at least one adjusting slot (32) extending obliquely to the path of motion (16). This is advantageous with regard to an embodiment which is as compact as possible and as insusceptible to dirt as possible.

The above and further aspects of the invention will become apparent from the embodiments described below and are clarified with reference to these embodiments.

The invention will be further described with reference to embodiments shown in the drawings to which, however, the invention is not restricted.

FIG. 1 shows part of a personal care apparatus 1. The personal care apparatus 1 is intended and designed for the treatment of areas of humans skin; namely for the removal of skin residues and skin impurities by a suctorial action on the areas of skin in question.

Figure 5:
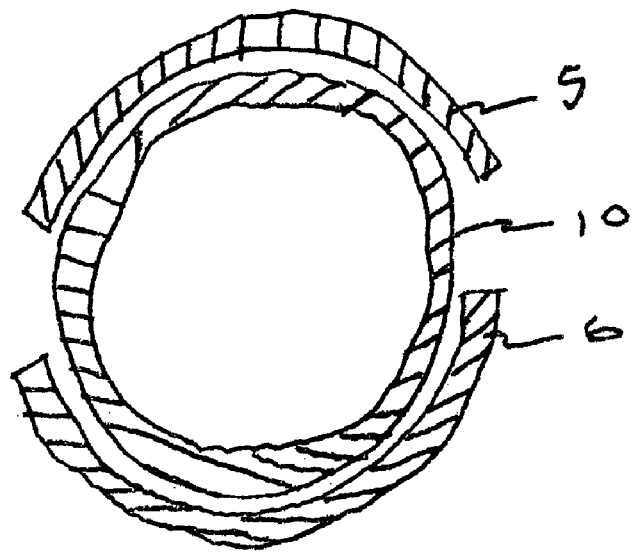
FIG. 5 shows a cross sectional view of the suction nozzle configuration of FIG. 1 in the same manner, showing details of retaining jaws in accordance with an embodiment of the present device.

The personal care apparatus 1 has a housing 2. The housing 2 is provided with a passage 3 which is intended and designed to hold a suction nozzle configuration 4. To support the fixing of the suction nozzle configuration 4 in the personal care apparatus 1, retaining jaws 5 and 6 connected to the housing 2 are provided which have a circular arc shape which is not evident from FIG. 1. FIG. 5 shows a cross sectional view, taken along sectional lines A-A shown in FIG. 1, of the suction nozzle configuration of FIG. 1 in the same manner, showing details of retaining jaws 5 and 6 in accordance with an embodiment of the present device. As shown, the retaining jaws 5 and 6 are provided with a circular arc shape that extends in a direction perpendicular to the path of motion shown in FIG. 1.

Figure 1:
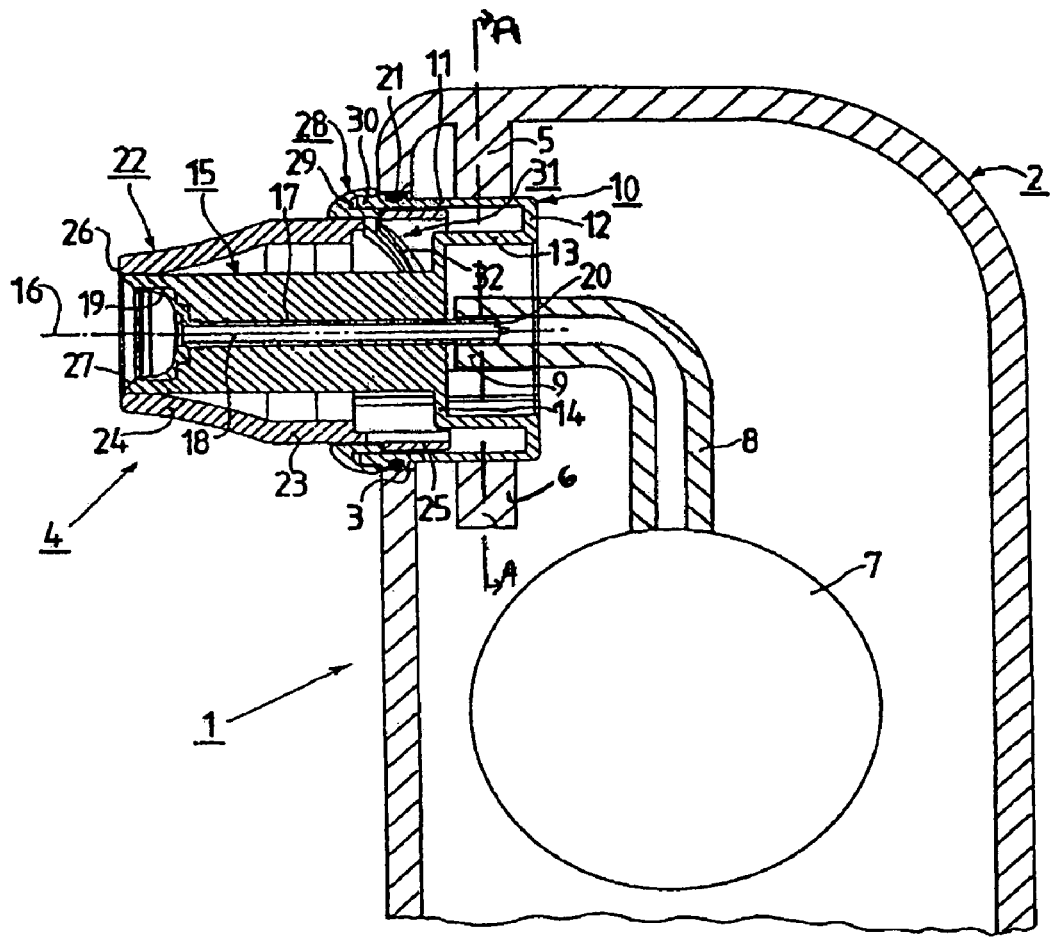
FIG. 1 shows partly diagrammatically in a cross-section a personal care apparatus in a first embodiment of the invention with a suction nozzle configuration according to a first embodiment of the invention, with two suction nozzles of the suction nozzle configuration occupying a first position relative to each other.

The personal care apparatus 1 comprises an air pump 7, which is only shown diagrammatically in FIG. 1. Protruding from the air pump 7 is an oblique tubular suction port 8 whose end 9, facing away from the air pump, is located between the retaining jaws 5 and 6 and adjacent to the passage 3. By means of the suction port 8, a suction action may be generated in the suction nozzle configuration 4, which has an air connection via the suction port 8 with to the air pump 7.

The suction nozzle configuration 4 comprises a tub-type base part 10 which comprises a hollow-cylindrical external wall 11 and a base wall 12 and a hollow-cylindrical internal wall 13 rising from the base wall 12 and running parallel to the hollow-cylindrical external wall 11. The tub-type base part 10 is integrally connected via a ring-shaped connecting wall 14 to an internal suction nozzle 15 of the suction nozzle configuration 4. The internal suction nozzle 15 comprises a bore 17 running parallel to an axis 16. The bore 17 holds a suction tube 18 which is integrally connected at its free end to a suction funnel 19. At the end 20 of the suction tube 18 facing away from the suction funnel 19, the suction tube 18 is connected to the suction port 8, which connection is as airtight as possible. It should also be mentioned that the tub-type base part 10, which hence forms a component of internal suction nozzle 15, is retained in the area of its hollow-cylindrical external wall 11 by means of the retaining jaws 5 and 6 and is also retained by means of the housing 2, a sealing ring 21 accommodated in a recess in the hollow-cylindrical external wall 11 being provided between the housing 2 and the hollow-cylindrical external wall 11. In this way, the retaining jaws 5 and 6 and the housing 2 each form a holding part of the personal care apparatus 1, with the internal suction nozzle 15 having a fixed connection to the holding parts 2, 5 and 6.

The suction nozzle configuration 4 also has an external suction nozzle 22. The external suction nozzle 22 essentially comprises a hollow-cylindrical center part 23, a front part 24 tapering relative to the center part 23, and a hollow-cylindrical rear part 25, said three parts 23, 24 and 25 being connected together in one piece.

In the area of the free end of the front part 24 of the external suction nozzle 22, the circular suction section 26 of the external suction nozzle 22 is provided for interaction with areas of skin. The is the circular-shaped suction section 27 of the internal suction nozzle 15 is provided for interaction with areas of skin in the area of the free end of the internal suction nozzle 15. As is evident from FIGS. 1 and 2, the external suction nozzle 22 and the internal suction nozzle 15 have suction sections 26 and 27 of different sizes. In this case, the suction sections 26 and 27 of different sizes run vertically to the axis 16. This is not absolutely necessary, because the suction sections 26 and 27 may alternatively be designed to run obliquely to the axis 16. In a plan view of the suction sections 26 and 27, i.e. in a direction perpendicular to the suction sections 26 and 27 and hence parallel to the axis 16, the suction section 27 of the internal suction nozzle 15 lies within the suction section 26 of the external suction nozzle 22 having a larger suction section. As is evident from FIG. 1, the two suction sections 26 and 27 of the suction nozzles 22 and 15 in the personal care apparatus 1 face away from the rest of the personal care apparatus 1.

In the personal care apparatus 1, the embodiment is advantageously designed such that the external suction nozzle 22 and the internal suction nozzle 15 are held adjustably in relation to each other along a path of motion and in this case in the direction of the axis 16, i.e. perpendicularly to their suction sections 26 and 27, and that by means of an adjustment of the two suction nozzles 22 and 15 in relation to each other one of these two suction nozzles 22 and 15 may be adjusted each time into an operating position permitting suctorial interaction with an area of the skin. In this case, the internal suction nozzle 15 with a smaller suction section 27 is connected to the retaining jaws 5 and 6 provided as holding parts and fixedly connected to the housing 2, and the external suction nozzle 22 with a larger suction section 26 has an adjustable connection to the internal suction nozzle 15. In this case, the external suction nozzle 22 is adjustably guided by guide means, (not shown) extending in the direction of the axis 16, i.e. two guide grooves extending in the direction of the axis 16 and two guide ribs extending in the direction of the axis 16 and projecting into the guide grooves parallel to the axis 16. In the case of an adjustment parallel to the axis 16 of the external suction nozzle 22 in relation to the internal suction nozzle 15, the hollow-cylindrical rear part 25 of the external suction nozzle 22 slides along the hollow-cylindrical external part 11 of the base part 10 of the internal suction nozzle 15.

For the adjustment of the external suction nozzle 22 in relation to the internal suction nozzle 15, the suction nozzle configuration 4 is provided with an adjusting ring 28 which is perpendicular to the path of motion of the external suction nozzle 22 and hence perpendicular to the axis 16 and parallel to the suction sections 26 and 27, and which is rotatably held at the internal suction nozzle 15, i.e. in that the adjusting ring 28 is provided with a circular groove 29 with which the adjusting ring 28 is placed on the free end 30 of the hollow-cylindrical external wall 11 of the base part 10 of the internal suction nozzle 15. Between the adjusting ring 28 and the external suction nozzle 22, adjusting means 31 are provided for the adjustment of the external suction nozzle 22. In this case, the adjusting means 31 are formed by a pin-slot configuration, which in this case has two adjusting slots 32 having an inclined gradient in relation to the suction sections 26 and 27 and to the adjusting ring 8, of which only one adjusting slot may be seen in FIGS. 1 and 2. Here, the adjusting slots 32 are provided in the hollow-cylindrical rear part 25 of the external suction nozzle 22. A pin protruding from the adjusting ring 28 in a radial direction projects into each of the two adjusting slots 32, but this is not evident in FIGS. 1 and 2. These kinds of pin-slot configurations for adjusting purposes have been known per se for a long time.

Figure 2:
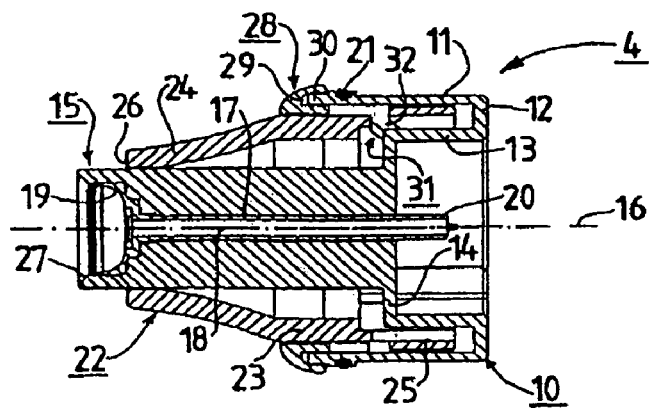
FIG. 2 shows the suction nozzle configuration also shown in FIG. 1, with the two suction nozzles occupying a second relative position to each other.

As is evident from FIGS. 1 and 2, it is facilitated by means of the suction nozzle configuration 4 that, if desired, a person using the personal care apparatus 1 can activate in each case the desired suction nozzle with the desired suction section in a simple way for applicational purposes. In the operational situation shown in FIG. 1, the external suction nozzle 22 is in its forward operating position further away from the rest of the personal care apparatus 1, i.e. in a forward operating position, which renders it possible to bring the external suction nozzle 22 with the larger suction section 26 into an active connection with an area of skin. In the operating situation shown in FIG. 2, which is obtained by twisting the adjusting ring 28 and the displacement of the external suction nozzle 22 effected by this in the direction of the rest of the personal care apparatus 1, the internal suction nozzle 15 with the smaller suction section 27 can be brought into an active connection with a section of skin, with the pushed-back external suction nozzle 22 and its larger suction section 26 exerting no suctorial influence on the area of skin in question.

With the suction nozzle configuration according to FIGS. 1 and 2, it is advantageous if the internal suction nozzle 15 is embodied highly polished in the area of the suction section 27 and if the external suction nozzle 22 in the area of the suction section 26 has a rougher surface than the highly polished embodiment of the suction section 27 of the internal suction nozzle 15. With the operating position shown in FIG. 1, it is achieved thereby that the external suction nozzle 22 with its suction section 26 has a suctorial action on an area of skin, with, after the suction of an area of skin by means of the highly polished suction section 27 of the internal suction nozzle 15, a good seal being achieved between the skin and the highly polished suction section 27.

With the embodiment of the personal care apparatus 1 according to FIGS. 1 and 2 or the suction nozzle configuration 4 according to FIGS. 1 and 2, it is achieved in a simple way by means of a change-over procedure with the aid of the adjusting rings 28 that different suction sections 26 and 27 of two suction nozzles 22 and 15 may be put into action, without the suction nozzle configuration 4 having to be removed from the personal care apparatus 1 and namely because a simple twisting of the adjusting ring 28, suffices to put into action the desired suction nozzle 22 or 15 in each case. A change-over procedure of this type may also be performed during operation, i.e. during the suction.

Figure 3:
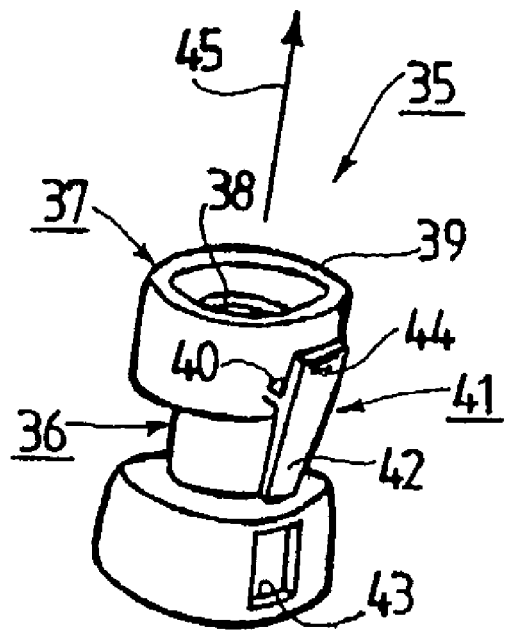
FIG. 3 shows in an oblique view a suction nozzle configuration in a second embodiment of the invention of a personal care apparatus according to a second embodiment of the invention, with two suction nozzles of the suction nozzle configuration occupying a first position relative to each other.
Figure 4:
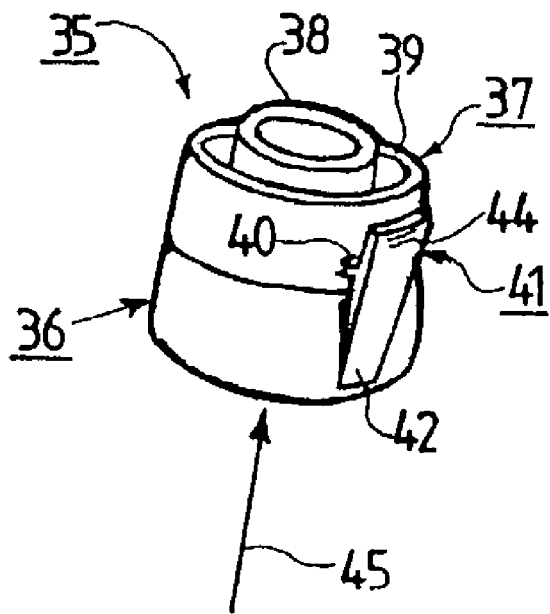
FIG. 4 shows the suction nozzle configuration of FIG. 3 in the same manner, with the two suction nozzles occupying a second position relative to each other.

FIGS. 3 and 4 show another suction nozzle configuration 35. The suction nozzle configuration 35 also has an internal suction nozzle 36 and an external suction nozzle 37. The internal suction nozzle 36 has a smaller suction section 38 and the external suction nozzle 37 has a larger suction section 39. The external suction nozzle 37 is guided movably on the internal suction nozzle 36. The external suction nozzle 37 is equipped with a locking lever 41 connected by a bar 40 to the external suction nozzle 37. In the area of one end 42, the locking lever 41 has a locking extension, not evident in FIGS. 3 and 4, which can snap into a locking recess 43 in the internal suction nozzle 36, as shown in FIG. 4. Actuating the locking lever 41 in the area of its other end 44 makes it possible to move the locking extension out of the locking recess 42, after which the external suction nozzle 37 may be moved away from the internal suction nozzle 36 in the direction of an arrow 45 to achieve the operating situation shown in FIG. 3.

With the embodiment of the suction nozzle configuration 35 according to FIGS. 3 and 4, it is again possible in a simple way to put different suction sections 38 and 39 of different suction nozzles 36 and 37 into action.

Figure 6:
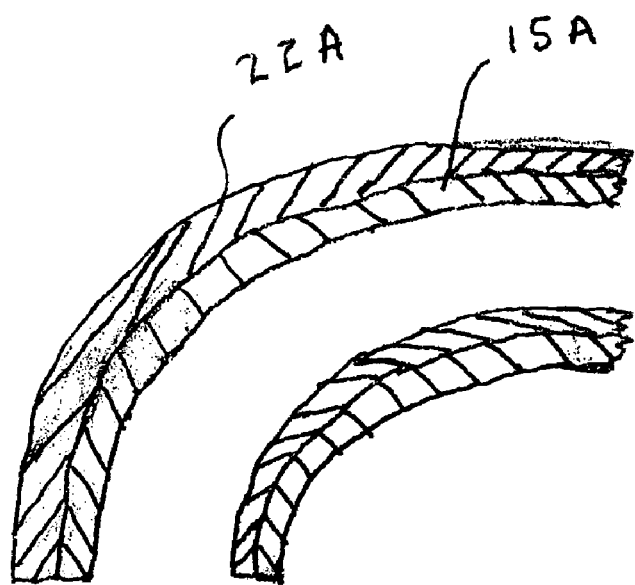
FIG. 6 shows a suction nozzle configuration in accordance with an embodiment of the present system.

With the above-described suction nozzle configurations 4 and 35, the suction nozzles 15 and 22 or 36 and 37 are each essentially arranged and designed coaxially to the axis 16 or the arrow 45 and are each held adjustably in relation to each other along a straight path of motion corresponding to the axis 16 or corresponding to the arrow 45. This does not necessarily have to be the case, because in one alternative embodiment of a suction nozzle configuration shown in FIG. 6, the suction nozzles 15A and 22A in this suction nozzle configuration may also have a circular-arc shape and be held adjustably in relation to each other according to this circular-arc shape. It should also be mentioned that an embodiment without an adjusting ring is also possible, with it being possible to provide a pin-slot configuration between the external suction nozzle 22 and the base part 10 of the internal suction nozzle 15, by means of which, the external suction nozzle 22 can be adjusted in the direction of the path of motion for the external suction nozzle 22 if the external suction nozzle 22 is twisted by at least two fingers.

The invention claimed is:

1. A personal care apparatus with an air pump and with a suction nozzle configuration, which has an air connection to the air pump and which has at least two suction nozzles, having suction sections of different sizes, wherein, in a plan view of the suction sections, the suction section of an internal suction nozzle lies within the suction section of an external suction nozzle having a larger suction section, and wherein all suction sections of the suction nozzles face away from the rest of the personal care apparatus, and wherein with the suction nozzles are held adjustably in relation to each other along a path of motion, and wherein at least one of said suction nozzles is displaceable into an operating position permitting suctorial interaction with an area of the skin by means of an adjustment of the suction nozzles in relation to each other, wherein the external suction nozzle is equipped with a locking lever connected by a bar to the external suction nozzle, wherein the suction nozzles are held in relation to each other by the locking lever if the locking lever is in a locking position, and wherein the suction nozzles are adjustably in relation to each other along a path of motion if the locking lever is not in a locking position.

2. The personal care apparatus as claimed in claim 1, wherein the suction nozzle configuration has only two suction nozzles, of which the internal suction nozzle with the smaller suction section has a fixed connection to at least one holding part of the personal care apparatus, and of which the external suction nozzle with a larger suction section has an adjustable connection to the internal suction nozzle.

3. The personal care apparatus as claimed in claim 2, wherein an adjusting ring which is essentially perpendicular to the path of motion is rotatable supported on the internal suction nozzle.

4. The personal care apparatus as claimed in claim 1, wherein the at least two suction nozzles have a circular-arc shape and are configured to be held adjustably in relation to each other according to the circular-arc shape.

5. The personal care apparatus as claimed in claim 1, comprising a plurality of retaining jaws affixed to the personal care apparatus and configured to fixedly retain the one suction nozzle that lies within the suction section of the suction nozzle having the larger suction section, wherein each of the plurality of retaining jaws have a circular-arc shape extending in a direction perpendicular to the path of motion.

6. A suction nozzle configuration for a personal care apparatus, which suction nozzle configuration has at least two suction nozzles with suction sections of different sizes, wherein, in a plan view of the suction sections, the suction section of an internal suction nozzle lies within the suction section of an external suction nozzle having a larger suction section, and wherein all suction sections of the suction nozzles face away from the rest of the personal care apparatus, and wherein the suction nozzles are held adjustably in relation to each other along a path of motion, and wherein it is possible to adjust at least one of said suction nozzles into an operating position permitting suctorial interaction with an area of the skin by means of an adjustment of the suction nozzles in relation to each other, wherein the external suction nozzle is equipped with a locking lever connected by a bar to the external suction nozzle, wherein the suction nozzles are held in relation to each other by the locking lever if the locking lever is in a locking position, and wherein the suction nozzles are adjustably in relation to each other along a path of motion if the locking lever is not in a locking position.

7. The suction nozzle configuration as claimed in claim 6, wherein the suction nozzle configuration has only two suction nozzles, of which the internal suction nozzle with a smaller suction section has a fixed connection to at least one holding part in the personal care apparatus, and of which the external section suction nozzle with a larger suction section is held adjustably on the internal suction nozzle.

8. The suction nozzle configuration as claimed in claim 7, wherein an adjusting ring extending perpendicularly vertically to the path of motion is rotatably supported on the internal suction nozzle.

9. The suction nozzle configuration as claimed in claim 6, wherein the at least two suction nozzles have a circular-arc shape and are configured to be held adjustably in relation to each other according to the circular-arc shape.

10. The suction nozzle configuration as claimed in claim 6, comprising a plurality of retaining jaws affixed to the personal care apparatus and configured to fixedly retain the one suction nozzle that lies within the suction section of the suction nozzle having the larger suction section, wherein each of the plurality of retaining jaws have a circular-arc shape extending in a direction perpendicular to the path of motion.

11. A suction nozzle configuration for a personal care apparatus, which suction nozzle configuration has at least two suction nozzles with suction section of different sizes, wherein the suction section of an internal suction nozzle lies within the suction section of an external suction nozzle having a larger suction section, and wherein all suction sections of the suction nozzles face away from the rest of the personal care apparatus, and wherein the suction nozzles are held adjustably in relation to each other along a path of motion, and wherein it is possible to adjust at least one of said suction nozzles into an operating position permitting suctorial interaction with an area of the skin by means of an adjustment of the suction nozzles in relation to each other, wherein the external suction nozzle is equipped with a locking lever connected by a bar to the external suction nozzle, wherein the suction nozzles are held in relation to each other by the locking lever if the locking lever is in a locking position, and wherein the suction nozzles are adjustably in relation to each other along a path of motion if the locking lever is not in a locking position.

12. The suction configuration as claimed in claim 11, wherein the at least two suction nozzles have a circular-arc shape and are configured to be held adjustably in relation to each other according to the circular-arc shape.

13. The personal care apparatus as claimed in claim 11, wherein the internal suction nozzle is provided with a locking recess, and the locking lever is in the locking position when the locking lever is engaged in the locking recess.

14. The suction nozzle configuration as claimed in claim 11, comprising a plurality of retaining jaws affixed to the personal care apparatus and configured to fixedly retain the one suction nozzle that lies within the suction section of the suction nozzle having the larger suction section, wherein each of the plurality of retaining jaws have a circular-arc shape extending in a direction perpendicular to the path of motion.

* * * * *